US008527244B2

(12) United States Patent
Shin (10) Patent No.: US 8,527,244 B2
(45) Date of Patent: Sep. 3, 2013

(54) GENERATING MODEL DATA REPRESENTING A BIOLOGICAL BODY SECTION

(75) Inventor: Hoen-oh Shin, Hannover (DE)

(73) Assignee: Medizinische Hochschule Hannover (MMH), Hannover (DE)

( * ) Notice: Subject to any disclaimer, the term of this patent is extended or adjusted under 35 U.S.C. 154(b) by 361 days.

(21) Appl. No.: 12/850,235

(22) Filed: Aug. 4, 2010

(65) Prior Publication Data

US 2012/0035888 A1 Feb. 9, 2012

(51) Int. Cl.
*G06F 17/50* (2006.01)
*G05B 19/18* (2006.01)

(52) U.S. Cl.
USPC ................................ 703/1; 700/57

(58) Field of Classification Search
USPC .............................. 703/1; 700/57
See application file for complete search history.

(56) References Cited

U.S. PATENT DOCUMENTS

| 8,073,216 | B2 * | 12/2011 | Dawant et al. | 382/128 |
| 8,407,067 | B2 * | 3/2013 | Uthgenannt et al. | 705/2 |
| 2010/0111370 | A1 * | 5/2010 | Black et al. | 382/111 |

OTHER PUBLICATIONS

Shin, NPL, "Pre-operated planning of complex midfacial fractures using CT data: formation of a virtual model by registration of a reference skull", May 12, 2010.*
Shin, NPL, "Preoperative planning of complex midfacial fractures Generation of a virtual surgical model by registration of a "standard" skull", Feb. 8, 2010.*
Stefan Zachow, NPL, "Computer-Assisted Planning in Cranio-Maxillofacial Surgery", 2006.*
T Lange, NPL, "Registration of different phases of contrast enhanced CT/MRI data for computer assited liver surgery planning: Evaluation of state or the art methods", 2005.*
Piotr Borkowski, NPL, "Geometrical modeling of knee joint including anatomic properties", 2006.*
Gassner et al., "Cranio-maxillofacial trauma: a 10 year review of 9543 cases with 21 067 injuries", Journal of Cranio-Maxillofacial Surgery, vol. 31, pp. 51-61 (2003).
Rueckert et al., "Nonrigid Registration Using Free-Form Deformations: Application to Breast MR Images", IEEE Transactions on Medical Imaging, vol. 18, pp. 712-721 (1999).
Shin et al., "Preoperative planning of complex midfacial fractures: Generation of a virtual, surgical model by registration of a "standard" skull", Abstract B-527, The ECR 2010 Book of Abstracts (European Society of Radiology, 2010).
Shin et al., "Pre-operated planning of complex midfacial fractures using CT data: Formation of a virtual model by registration of a reference skull", Deutscher Rontgenkongress, (DRK, Berlin, May 2010).
Thevenaz, "Optimization of Mutual Information for Multiresolution Image Registration", IEEE Transactions on Medical Imaging, vol. 9, pp. 2083-2099 (2000).
Unser, "Splines: A Perfect Fit for Signal and Image Processing", IEEE Signal Processing Magazine, pp. 22-38 (1999).
Zachow et al., "Computer-Assisted Planning in Cranio-Maxillofacial Surgery", Journal of Computing and Information Technology—CIT 14, pp. 53-64 (2006).

* cited by examiner

*Primary Examiner* — Omar Fernandez Rivas
*Assistant Examiner* — Angel Calle
(74) *Attorney, Agent, or Firm* — Caesar, Rivise, Bernstein, Cohen & Pokotilow, Ltd.

(57) ABSTRACT

A method of generating model data representing a body section of a biological organism, like e.g., a head or part thereof, a joint, or soft tissue, includes the steps of providing object data representing a first portion of the body section, providing standard data representing a complete standard body section, and subjecting the standard data to a registration process, wherein the model data to be generated are created by adapting the standard data to the object data, said model data representing the first portion of the body section and a second portion of the body section.

21 Claims, 5 Drawing Sheets

FIG. 9

GENERATING MODEL DATA REPRESENTING A BIOLOGICAL BODY SECTION

FIELD OF THE INVENTION

The present invention relates to a method of generating model data representing a body section of a biological organism, in particular for creating a 3D model of the body section, like e.g., a skull. Furthermore, the present invention relates to a computer program product residing on a computer-readable medium and including a program code for carrying out the method of generating model data and to a computer device comprising a computer-readable storage medium containing program instructions for carrying out the method of generating model data. Applications of the invention are present in the fields of creating virtual or real models of biological body sections or parts thereof, used e.g., for operative planning, supporting surgical operations and/or making implants.

BACKGROUND OF THE INVENTION

Computer-assisted surgery (CAS) is a generally known and practically used surgery method, wherein a surgical operation is planned and/or conducted using a 3D model of a body section to be treated. In particular, the 3D model can be used for planning the steps of a surgical operation, e.g., the motion and adjustment of surgical tools or implants, for monitoring the surgical operation, or for constructing a real 3D implant. Typically, the 3D model can be generated on the basis of image data collected with medical imaging of a patient, e.g., by an image registration of computer tomography (CT) data of the body section with CT data of a certain portion of the body section.

Image registration (or: registration, image alignment) is a data processing method, wherein different sets of image data are transformed into one common coordinate system. The different sets of real image data are collected e.g., with different sensors, at different times and/or from different viewpoints. Typically, a first set of image data (target image) is adapted to a second set of image data (reference image), both covering the same region of investigation. The transformation or adaptation can be performed manually, interactively, semi-automatically or automatically. The automatic registration uses a numerical registration process (registration algorithm). Conventional applications of image registration are restricted to the transformation of data covering the same region of investigation.

If image data of a complete body section are not available, e.g., due to a destruction after an accident or a disease, or due to a congenital defect, generating model data for a 3D model requires a completion of the collected real image data with reconstructed data. As an example, CAS applications in Cranio-Maxillar-Facial surgery (CMF surgery) may require a reconstructed patient 3D model for obtaining complete skull image data. With one-sided defects, completion of collected data can be obtained by a simple mirroring of the healthy half to the pathological half of the skull. However, with defects on both sides of the skull or with asymmetric body sections, a reconstruction is required, which conventionally comprises manual or semi-automatic procedures using reference points and reference planes in a reference image selected by a surgeon (see S. Zachow et al. in "Journal of Computing and Information Technology—CIT 14" vol. 1, 2006, p. 53-64).

Those conventional procedures are time-consuming and prone to failures. As a further disadvantage, the quality of the 3D model thus obtained essentially depends on the experience of the surgeon.

OBJECTIVE OF THE INVENTION

The objective of the invention is to provide an improved method of generating model data representing a body section of a biological organism, said method being capable of avoiding disadvantages of conventional techniques. In particular, the objective is to provide a method which enables generating model data with reduced time expenditure for the user, with improved quality and/or with an increased independency of the surgeon's experience.

SUMMARY OF THE INVENTION

The above objective is solved by a method of the invention. According to a first aspect of the invention, a method of generating model data representing a body section of a biological organism is provided wherein standard data representing a complete standard body section are registered to object data representing a first portion of the body section only. The registration yields adapted or transformed standard data which represent the model data to be obtained. Advantageously, the model data created by adapting the standard data to the object data represent the complete body section including both the first portion and a second complementary portion of the body section.

According to further aspects of the invention, a computer program product residing on a computer-readable medium and including a program code for carrying out the method of the above first aspect and a computer device comprising a computer-readable storage medium containing program instructions for carrying out the method of the above first aspect are provided.

Contrary to conventional methods of generating model data, the inventive method represents a universal, automatic approach for creating virtual or real models of the body section under investigation or parts thereof. High quality models can be obtained in a reproducible manner independently of the user. In particular, the inventive method allows for automatic modeling of individual prosthesis and preoperative planning for reconstructive surgery within a shortened processing time without user interaction of e.g., 5 hours or below. Furthermore, individual prosthesis correction or reconstruction of body defects acquired from traumatic injuries, congenital birth defects and surgical ablation of cancer can be obtained.

The standard data are registered automatically, i.e., without a user interaction, to the object data which include information on the incomplete body section only, e.g., a fragment or partial portion (first portion) thereof. The inventor has found that equal body sections, like e.g., the skulls of human beings, have a high degree of inherent similarity. Therefore, according to the invention, the objective information included in the standard data can be used for completing a particular body section. Thus, the inventive registration with the adaptation of the standard data content representing the first portion simultaneously results in a transformation of the remaining standard data content representing the remaining portion of the body section (second portion). This transformation yields improved reconstruction results of the complete body section. Contrary to conventional registration methods, the standard data and the object data do not represent the same region of investigation, but the standard data cover a larger area of the body section than the object data.

As an advantage, the invention can be applied with any part of a body of a biological organism, preferably of a human or animal body. Thus, the term "body section" may refer to any anatomical region of the body, like e.g., a head or part thereof, a joint, e.g., a knee joint, and/or a soft tissue portion. According to a particularly preferred application of the invention, the body section is a skull of a human patient. The body section may refer to solid (e.g., bones, skull) and/or soft parts (e.g., soft tissue, muscles) of the body.

The "object data" include a data set obtained from sensed data, e.g., data collected with a sensor device, preferably with an imaging device, like e.g., a CT or MRT device. The object data include an image representation of the real body section of interest (first portion of a complete body section). The first portion of a complete body section may consist of a continuous part or at least two separate parts of the body section.

The "standard data" comprise a data set including an image representation of a standard body section and being provided from a standard data base, like e.g., a data storage including data from a plurality of real subjects, e.g., healthy humans (real standard data) and/or data derived from the real standard data (virtual standard data) by at least one of mirroring or enhancing structural elements, e.g., by manually editing structural elements. The standard body section covers the complete body section, i.e., corresponding to the real body section of interest and further missing parts thereof to be reconstructed (second portion). The second portion of the complete body section also may consist of a continuous part or at least two separate parts of the body section. According to the terms used in conventional registration techniques, the standard data are the target image, which is adapted to a reference image provided by the object data. The "model data", i.e., the transformed standard data comprise the data set to be obtained, including an image representation of the body section of interest.

Any of the image representations (or: topographic representations) include data with spatial coordinates, e.g., intensity values for each spatial point of the body section, or with spatial frequency coordinates. Typically, the above data are volume data, in particular 3D image data.

According to advantageous embodiments of the invention, the object data are provided by subjecting the collected data to at least one of a masking and a segmentation process. Individually or in combination, both processes facilitate the delimitation of the first and second portions. The collected data are object raw data representing the body section and covering the healthy or fixed first portion and the destroyed or even missing second portion.

With the masking process, parts of the object raw data are removed which are included in the second portion of the body section and which represent displaced parts of the body section or foreign parts. As an example, data representing skull and/or mandible parts being separated from the skull and displaced and/or foreign bodies are removed yielding masked raw data. In particular, displaced parts which have been moved from their natural location as a result of an accident cannot be used for supporting the inventive registration process. This masking process can be done manually or automatically using an image recognition algorithm.

With the segmentation process, the object raw data or the masked raw data are subjected to a thresholding process, which is preferably used for the registration of a body section with bone structure. Alternatively or additionally, the segmentation may include a filtering process, an edge detection, a contour detection and/or a shape matching process, which preferably used for the registration of a body section with soft tissue structure. Advantageously, the segmentation yields a defined boundary between the first portion to be kept fixed and the second portion of the body section to be reconstructed.

According to a further advantageous embodiment of the invention, the standard data are selected from a plurality of standard data sets included in the standard data base. Preferably, the particular standard data set is selected which has the largest similarity or a minimum difference compared with the object data. As an advantage, the selection provides an initial data set representing an optimum starting guess and thus reducing the calculation time needed for the registration process. At least one of various types of standard data bases can be used, like e.g., an electronic data storage, a reference table or an anatomical atlas. The standard data base includes data sets collected with real subjects having the body section of interest in a complete, unimpaired and/or healthy condition and/or data sets obtained from said collected data being additionally subjected to image processing algorithms, like e.g., mirroring and/or scaling.

With increasing number of data sets included in the data base, the subsequent registration process can be improved. Preferably, the data base includes at least 100 data sets, particularly preferred at least 500 data sets, like 1000 data sets or more, e.g., even 10000 data sets or more. However, in particular with the use of virtual standard data, it may be sufficient to use less than 100 data sets, e.g., 50 data sets, or even 30 or 20 data sets only.

Preferably, the selecting step includes analyzing a similarity measure being characteristic for a matching degree between the object data and each of the plurality of standard data sets, like the mutual information measure (see e.g., Thévenaz and M. Unser "Optimization of mutual information for multiresolution image registration" in "IEEE Trans. Image Process." vol. 9(12), 2000, p. 2083-2099). The standard data set is selected, which provides best matching with the object data.

Alternatively, the standard data can be constructed from at least two standard data sets included in the standard data base. As a preferred example, at least two standard data sets can be arithmetically averaged for providing a virtual standard data set.

An essential step of the inventive method is the registration of the standard data to the object data. Advantageously, conventional registration algorithms as known from textbooks or scientific publications can be used for conducting this transformation of the standard data. The registration process used according to the invention, may comprise a linear transformation (rigid registration) only, wherein the model data are obtained by at least one of translating, rotating, scaling and shearing of the standard data. The linear transformation can be iteratively optimized using e.g., a gradient descent process. The rigid registration results in a coarse alignment of the standard data to the object data only, which can be sufficient with particular applications of the invention and which results in a processing time reduction.

Alternatively, the registration process may comprise a non-linear transformation (non-rigid or elastic registration), wherein the standard data are subjected to a spatial transformation algorithm. Preferably, the spatial transformation algorithm is iteratively optimized using e.g., a gradient descent process. A preferred example of a spatial transformation algorithm used with the invention is a B-spline transformation (described e.g., by L. I. Rueckert et al. in "Nonrigid registration using free-form deformations: Application to breast MR images" in "IEEE Trans. Med. Imag." Volume 18(8), 1999, p.

712-721). The implementation of this embodiment is not restricted to the cited algorithms but rather possible with other optimization algorithms or transformations known in the art. The non-rigid registration has an advantage in terms of an improved alignment of details (local features) of the standard data.

According to a particularly preferred embodiment of the invention, both of the rigid and non-rigid registration processes are combined in a two step registration process. Firstly, the standard data selected from the database are subjected to the rigid registration, followed by the non-rigid registration of the rigid registration result. With the rigid registration, initial data for the non-rigid registration are improved, thus reducing the data processing time and improving the registration result.

As a further advantage, the invention is not restrictive with regard to the type of object data, which can be collected with any available imaging method. According to a preferred embodiment of the invention, the object data comprise 3D Computer Tomography (CT) or Magnetic Resonance (MR) image data of the body section of interest. CT or MR image data have advantages in terms of availability with practically used imaging devices and available image processing algorithms.

The inventive method of generating model data may be implemented before or during a surgical operation on the body section. Advantageously, in particular for planning an operation, the inventive model data generation method can be combined with an imaging step. During or immediately after the medical imaging for collecting the object data, the inventive standard data registration can be applied. According to this preferred embodiment of the invention, the method includes the step of collecting the object data, e.g., collecting 3D CT or MR image data.

The model data obtained with the invention represent a set of volume data, which can be used e.g., for controlling a motion of a surgical tool or for adapting an implant to the body section. The tool motion is planned or monitored in the coordinate system of the model data. For CAS techniques, the model data can be used without further processing. However, for evaluating the result of the model data generation, constructing at least one of a virtual and a real object model using the model data can be preferred. The virtual or real object model provides a picture of the body section, e.g., on a display device or as a real model, which facilitates a visual evaluation of the generated model data by the surgeon or the patient.

Depending on the requirements to the model data, a further data adjustment can be implemented according to a further embodiment of the invention. The data adjustment includes a model data editing process, wherein local features of the model data can be amended, e.g., manually amended by an interaction with the surgeon. The steps of constructing a virtual or real 3D model and subjecting the current model data to a (further) data adjustment can be iteratively repeated.

As a further essential advantage of the invention, the model data, possibly after the above data adjustment, can be used for making an implant. An implantation model is constructed, which covers the second (missing) portion of the body section or a part thereof. The implantation model is used for controlling a manufacturing process for prototyping the implant.

According to further applications of the invention, the model data can be subjected to further data processing steps including e.g., a recording or storing in a model data storage, displaying on a display device and/or transmitting to a distant location, e.g., via a network to a distant data base. Displaying the model data may comprises the above 3D model creation for visualization purposes, e.g., by 2D printing or 3D printing (rapid prototyping).

BRIEF DESCRIPTION OF THE DRAWINGS

Further details and advantages of the invention are described in the following with reference to the attached drawings, which show in.

DESCRIPTION OF THE PREFERRED EMBODIMENTS

Details of preferred embodiments of the inventive method are described in the following with particular reference to the features of providing the object data and standard data and registering the standard data to the object data. Features of collecting image data used as object raw data, e.g., features of collecting 3D CT or MR image data are not described as any imaging process can be used, which is conventionally known. Furthermore, features of implementing particular data processing steps are not described as far as they are known from available descriptions of the numerical data processing algorithms. The inventive method is conducted by implementing the method steps with a software program carried out on a computer device. Programming details are not described as they are known as such from conventional software tools. Exemplary reference is made to the reconstruction of a portion of the human skull, in particular at least one of the nasal bone, zygomatic bone and orbit walls or floor, which represents a preferred embodiment of the invention. However, it is emphasized that the application of the invention is not restricted to the generation of model data of skulls, but correspondingly possible with other body sections, like e.g., a joint.

Figure 1:
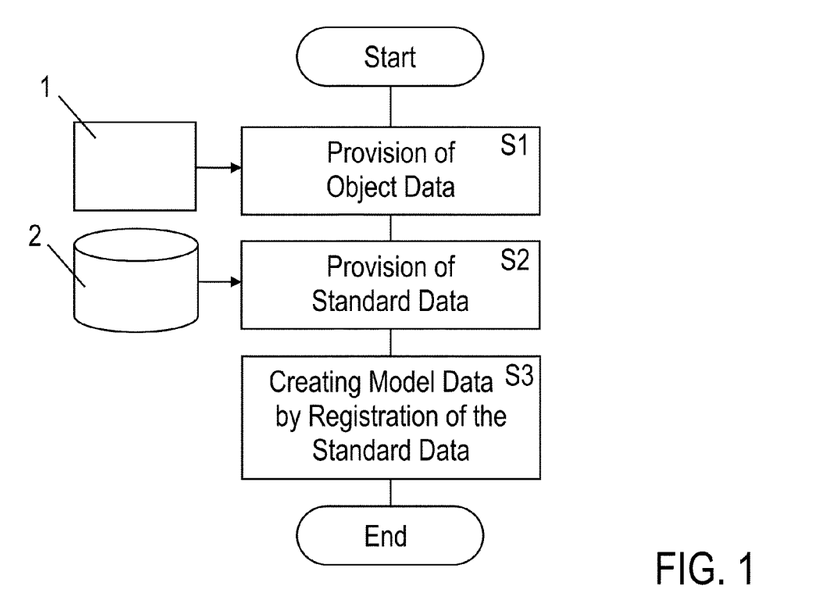
FIG. 1: a flow chart of the main steps of generating model data representing a body section of a biological organism according to the invention.

FIG. 1 schematically illustrates the main steps of the inventive method of generating model data including a first step S1 of providing object data, a second step S2 of providing standard data and a third step S3 of creating model data by a registration of the standard data to the object data.

Step S1 is conducted after a collection of patient raw data with a medical imaging device 1, like e.g., a CT scanner or MRI scanner. As an example, the head of a patient is imaged with a CT scanner 1, wherein a 3D image of the patient's skull is extracted from the CT image. As an example, the CT image consists of multi-detector-row CT data collected with a collimation of 0.625 mm and a reconstruction increment of 0.4 mm. Alternatively, a reconstruction increment of 1 mm may be sufficient. The scanning protocol practically used can be selected by the user, in particular in dependency on the imaging conditions and the type of imaging scanner device.

Figure 2:
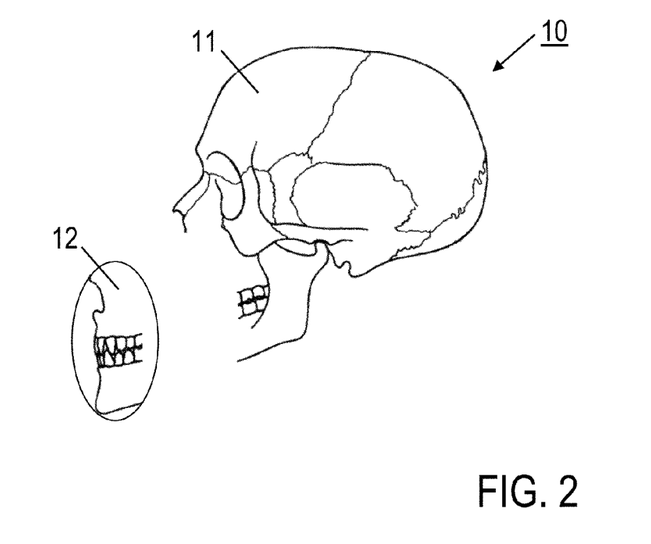
FIG. 2: a schematic illustration of a skull representing a body section to which the invention can be applied.

The imaged skull may be incomplete, e.g., as a result of an accident as schematically illustrated in FIG. 2. A first portion 11 of the skull 10 is complete and unimpaired by the accident, while a second portion 12 (schematically illustrated) is missed. The second portion 12 can be completely removed or represented in the patient raw data with a plurality of fragments. For creating object data, to which the standard data are to be registered, the patient raw data are subjected to data processing as described below with reference to FIG. 3.

With step S2, standard data are provided, which are selected from a database 2. A standard data set is selected, which has a maximum similarity with the object data as outlined below with reference to FIG. 3.

Step S3 of creating the model data comprises the application of a registration process to the standard data. The standard data are changed for adapting a reference skull to the object data as outlined below with reference to FIGS. 3 to 5.

Subsequently, a model generation and/or further data processing steps can be added depending on the particular requirements of the application.

Figure 3:
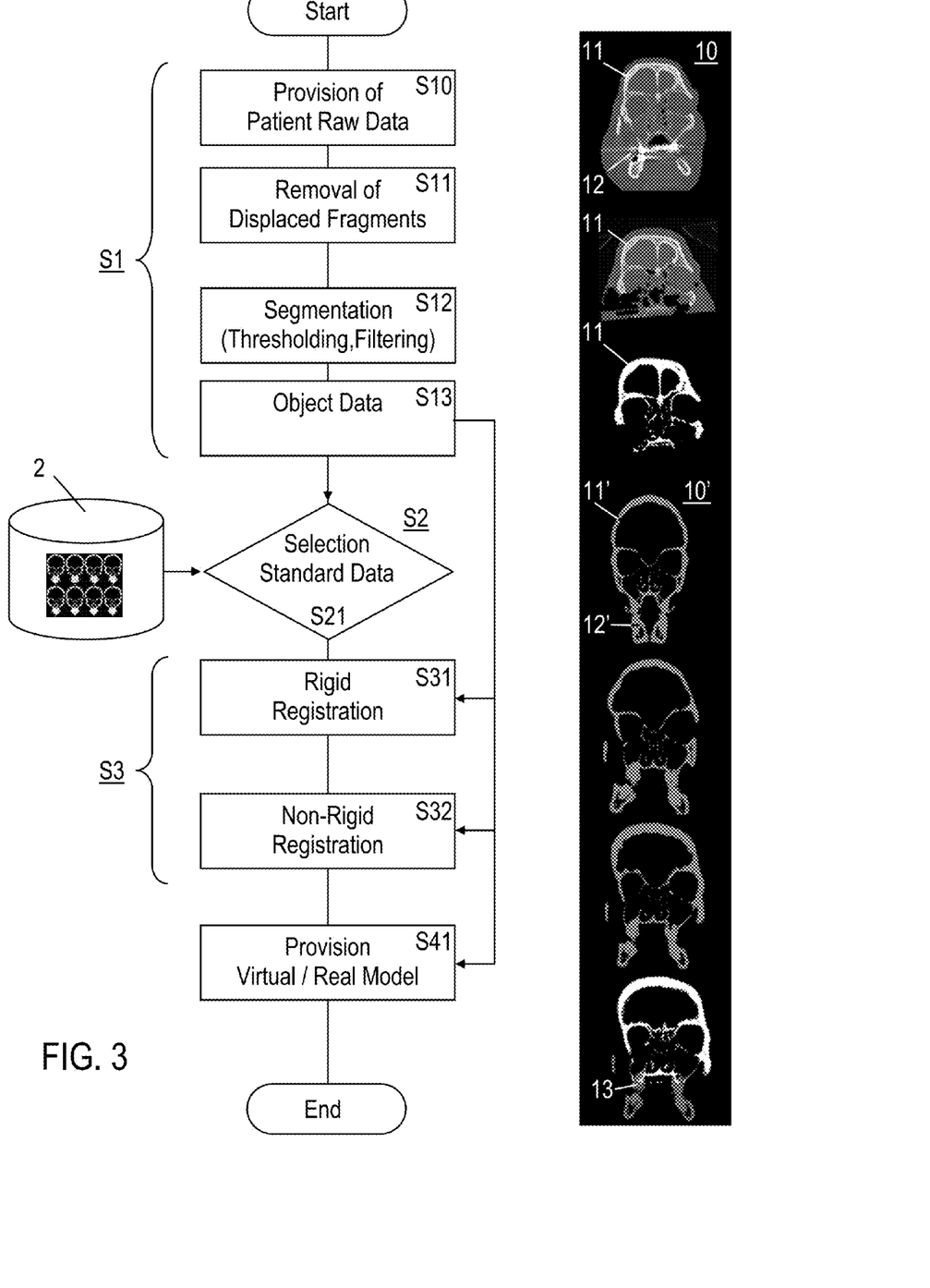
FIG. 3: a flow chart with further detailed steps of the model data generating method of FIG. 1.
Figure 7:
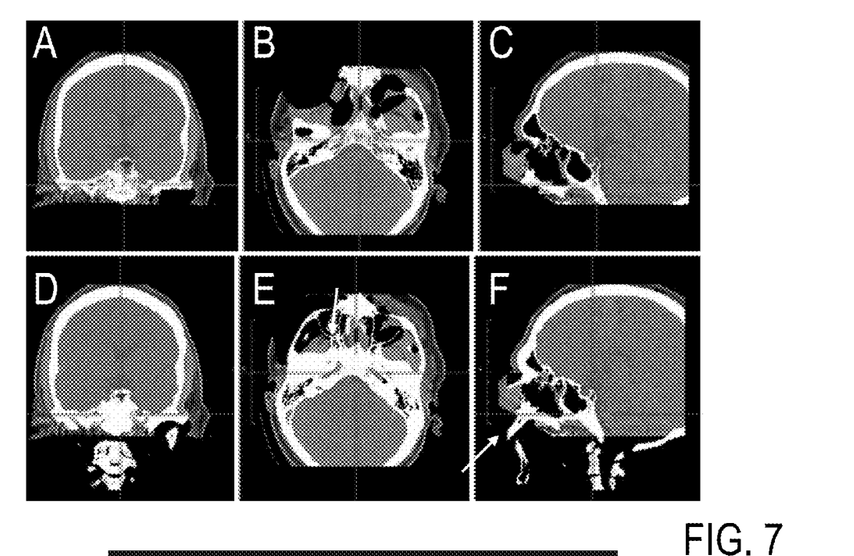
FIG. 7: exemplary skull image presentations of edited object data (A-C) and reconstructed model data (D-F) with different imaging planes.

Further details of the inventive method are illustrated in FIG. 3. On the right side of FIG. 3, exemplary illustrations of the image data are presented which are obtained with the steps in the flow chart of FIG. 3. Further detailed examples of image data are shown in FIG. 7. For providing the object data (step S1 in FIG. 1), firstly, patient raw data are provided (step S10). This can be done with an image data collection (medical imaging) immediately before the application of the inventive model data generation method or by transmitting patient raw data previously collected to a computer device including program instructions for carrying out the inventive model data generation method. The patient raw data comprise an image of the skull including the first portion 11 and the destroyed second portion 12.

Subsequently, displaced fragments, e.g., bone portions separated from the first portion, are removed with step S11. As an example, a manual removal of the displaced fragments and/or foreign bodies can be provided using a method of interactive editing. The displaced fragments and/or foreign bodies are marked on a display of the computer device e.g., by the surgeon. Subsequently, the marked portions are deleted from the patient raw data. As a result, image data essentially representing the first portion 11 are obtained as illustrated on the right side of step S11.

Subsequently, the image data are subjected to a segmentation (step S12). The segmentation includes a thresholding for extracting only those image data, which represent bone portions of the image. With CT images, this thresholding is simply implemented as the CT image density (intensity) of the bone portions strongly differs from the intensities of other parts of the head, e.g., the brain substance. Furthermore, so-called "flying pixels" are removed by a morphological filtering step included in step S12 resulting in the complete object data in step S13 (illustrated on the right side of step S13).

The provision of the standard data (step S2 in FIG. 1) comprises a selection of the standard data from the database 2 with step S21. The selection of the standard data is done by a comparison of the object data with the standard data sets in the database 2, wherein the "mutual information MI" is used as a similarity measure. The best matching skull 10' is selected (printed grey).

The mutual information MI is defined (see Thévenaz and M. Unser, cited above) as:

$$MI(\mu; I_F, I_M) = \sum_{m \in L_M} \sum_{f \in L_F} p(f, m; \mu) \log_2 \left( \frac{p(f, m; \mu)}{p_F(f) p_M(m; \mu)} \right)$$

where $L_F$ and $L_M$ are sets of regularly spaced intensity bin centers, p is a discrete joint probability, and $p_F$ and $p_M$ are a marginal discrete probabilities of the fixed and moving image, obtained by summing p over m and f, respectively. The joint probabilities are estimated using B-spline Parzen windows:

$$p(f, m; \mu) = \frac{1}{|\Omega_F|} \sum_{x_i \in \Omega_F} w_F \left( \frac{f}{\sigma_F} - \frac{I_F(x_i)}{\sigma_F} \right) \times w_M \left( \frac{m}{\sigma_M} - \frac{I_M(T_\mu(x_i))}{\sigma_M} \right),$$

where $w_F$ and $w_M$ represent fixed and moving B-spline Parzen windows. The scaling constants $\delta_F$ and $\delta_M$ are equal the intensity bin widths defined by $L_F$ and $L_M$. These follow directly from grey-value ranges of $I_F$ and $I_M$ and a user specified number of histogram bins |LF| and |LM|.

The standard data selection does not necessarily use the mutual information MI, but rather can be based on other similarity measures, like e.g., measures based on a sum of square differences, normalized correlation coefficients, normalized mutual information, or Kappa statistic.

As a result of the step S21, standard data representing an image of the complete skull 10' including the first and second portions 11', 12' are obtained. These standard data are registered to the object data in the following steps S31 and S32 (for details, see FIGS. 4 and 5).

Figure 4:
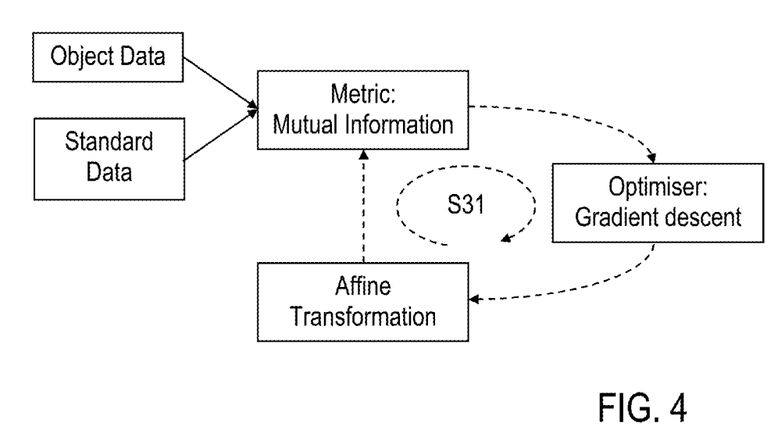
FIGS. 4 and 5: flow charts illustrating rigid and non-rigid registration processes used according to the invention.

With the rigid registration (step S31), the standard data are subjected to an affine transformation such that the similarity of the standard data with the object data (first portion 11) is improved. As shown in FIG. 4, the object data obtained with step S13 and the standard data obtained with step S21 are used as the input for the rigid registration (step S31). As a similarity measure, the mutual information MI (see above) can be used.

Generally, the affine transformation is defined as $$T\mu(x) = A(x-c) + t + c$$

wherein the transformation matrix A can be selected without restrictions. The image can be translated using the translation vector t, rotated around a center c of rotation, scaled and/or sheared. The parameter vector μ is formed by the matrix elements $a_{ij}$ of the transformation matrix A and the translation vector t. The matrix elements are optimized using a gradient descent method, which takes the search direction as a negative gradient of the cost function:

$$\mu_{k+1} = \mu_k - a_k g(\mu_k)$$

wherein $g(\mu_k) = \delta C/\delta_\mu$ is evaluated for a current position $\mu_k$. The gain factor $a_k$ can be selected e.g., by a line search or by using a predetermined function of k. Further details of the gradient descent method can be found in standard textbooks.

Figure 5:
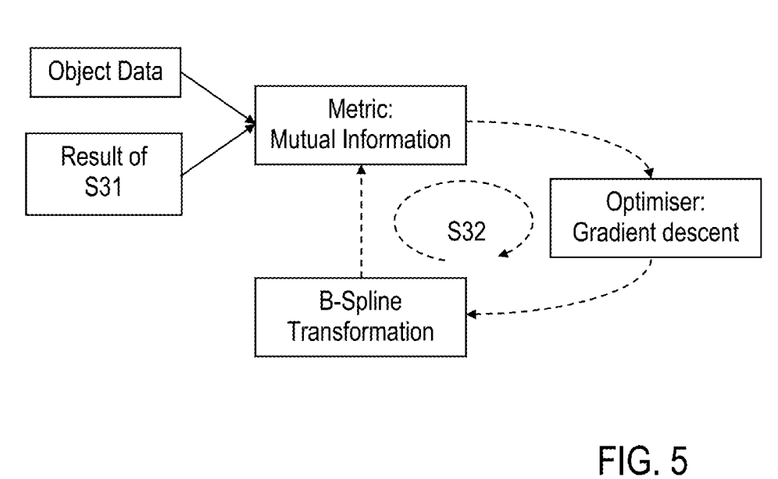

Subsequently, the result of the rigid registration, i.e., the linearly transformed standard data are subjected to the non-rigid registration to the object data (step S32 and FIG. 5). The non-rigid registration is based e.g., on a B-spline transformation as described e.g., by L. I. Rueckert et al., cited above. The B-spline transformation is represented by $$T_\mu(x) = x + \sum_{x_k \in N_x} p_k \beta^3(x - x_k)$$

wherein $x_k$ are control points, $\beta^3(x)$ is the cubic multidimensional B-spline polynomial [see Unser "Splines: A perfect fit for signal and image processing" in "IEEE Signal Process. Mag." vol. 16(6), 1999, p. 22-38), $p_k$ are B-spline coefficient vectors (i.e., the control point displacements), and Nx is a set of all control points within the compact support of the B-spline at x. The control points $x_k$ are defined on a regular grid, overlayed on the patient image. Again, the transformation parameters are optimized using the gradient descent method cited above.

As a result, the model data to be obtained are provided as the result of the non-rigid registration as illustrated on the right side of step S32.

Subsequently, a virtual and/or real model can be made with step S41. Depending on the applications of the invention, the model covers the whole body section, i.e. the skull 10 or only a part thereof, e.g., the second portion needed for completing the impaired skull.

For providing a virtual model of the second portion 12, the object data and the result of the non-rigid registration are used as input data. The object data (edited patient raw data) are subtracted from the registered standard data yielding a virtual model 13 (schematically illustrated with grey values in the FIG. 3 on the right side of step S41). Optionally, the virtual model construction can include a morphological filtering (opening).

On the basis of the virtual model, a surgical template for individual implant planning and plate contouring can be constructed. An implant can be made e.g., from a metal or plastics sheet or a scaffold being formed according to the contour of the virtual model data.

Figure 6:
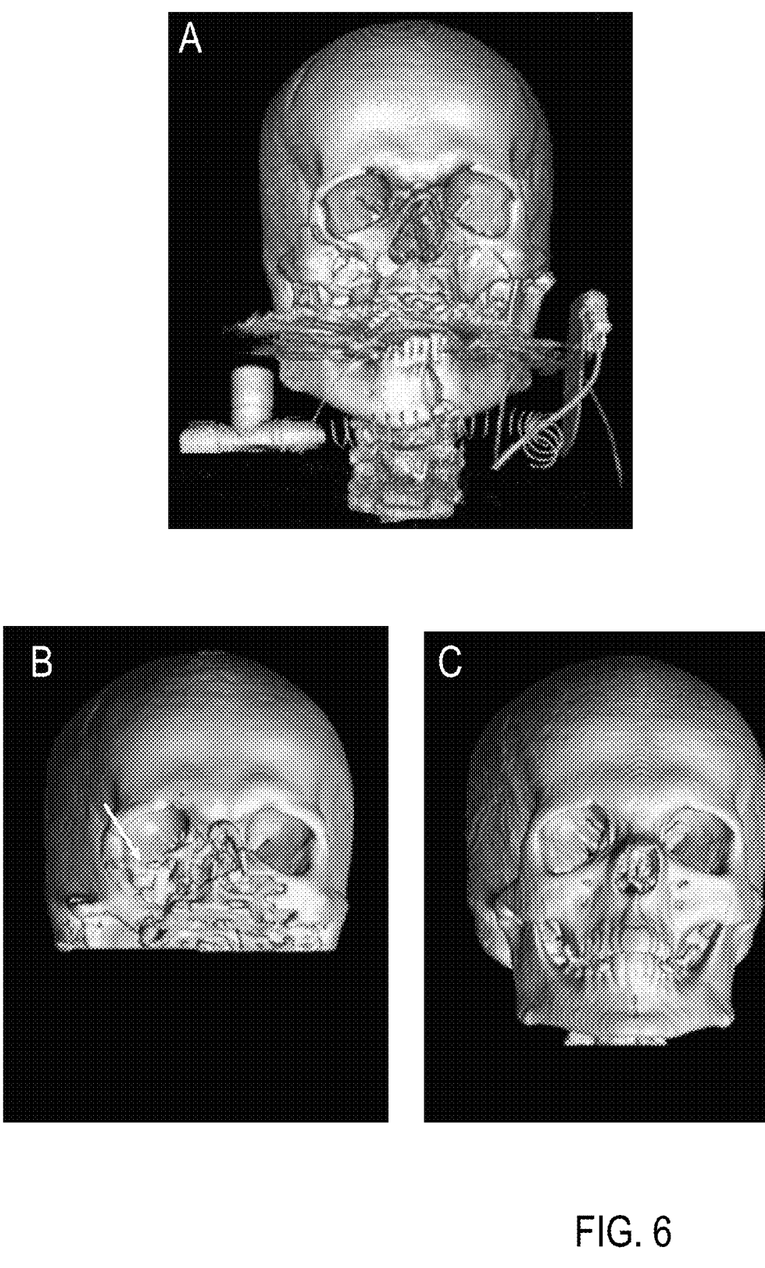
FIG. 6: exemplary skull image presentations at different phases of the inventive model data generating method.

The result of a concrete implementation of the inventive method is illustrated in FIG. 6, which shows the original patient raw data in FIG. 6A, the object data (fractures removed) in FIG. 6B and the complete virtual model in FIG. 6C. The patient raw data of FIG. 6A include image data of the skull including injured portions and medical devices, like e.g., stabilizing tools and intubation tools. In FIG. 6B, a part of the zygomatic bone on the right side of the patient's skull has been removed as well as a portion of the orbit floor (see arrow). Finally, FIG. 6C shows the complete model representing the reconstructed model data including in particular the reconstructed mandible parts and the reconstructed orbit floor. Test investigations of data with five healthy patients have shown extremely low differences between the real skull and a model generated according to the invention. The maximum deviation of model data and real data was equal or below 2.5 mm.

FIG. 7 illustrates a further example of reconstruction results obtained with the invention. Edited object data, i.e. the data provided with step S13 (see FIG. 3) are illustrated in FIGS. 7A to 7C with reference to frontal, transversal or side planes of a patient's data set. After the inventive registration, the model data of the same layers (FIGS. 7D to 7F) show the reconstruction of injured or removed bony parts, as it can be seen e.g., with the zygomatic bone in FIG. 7E or the nose bone in FIG. 7F (see arrows).

Figure 8:
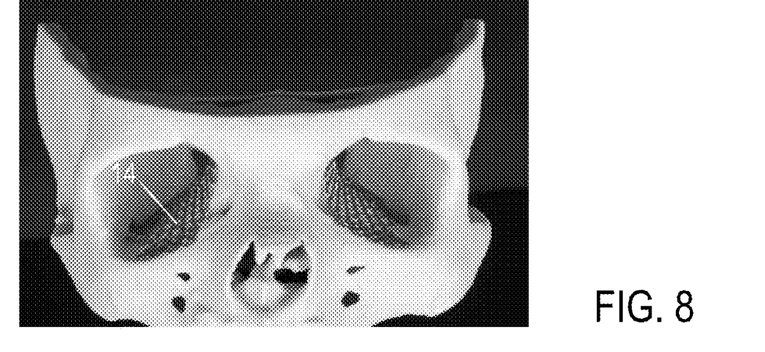
FIG. 8: an exemplary photographic image of an object model including reconstruction plates obtained with the invention.

According to the invention, a real object model can be constructed using the model data obtained with the inventive registration procedure. FIG. 8 illustrates an example of a real model including in particular implants 14 for reconstructing and stabilizing the orbit floor. With the real object model, the implants can be shaped and tested, before they are inserted with a surgical operation into the patient's head.

Figure 9:
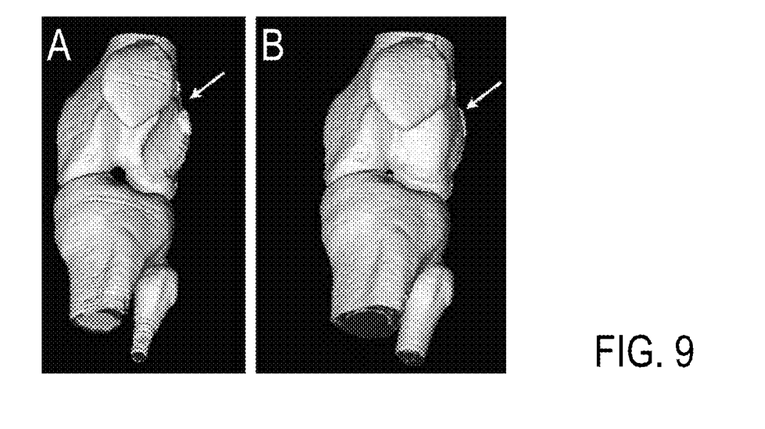
FIG. 9: exemplary knee joint image presentations of object data (A) and model data (B).

As an example of obtaining model data of another body section, FIG. 9 illustrates images representing a knee joint. According to FIG. 9A, the knee joint includes a defect as a result of an accident (see arrow). The defect has been reconstructed as shown in FIG. 9B. For reconstructing joint image data, the standard data used for the registration may comprise mirrored data of the second (healthy) joint of the patient or data from other patients.

The features of the invention in the above description, the drawings and the claims can be of significance both individually as well as in combination for the realization of the invention in its various embodiments.

What is claimed is:

1. A method of a method of generating model data representing a body section of a biological organism, comprising the steps of:
    providing object data representing a first portion of the body section,
    providing standard data representing a complete standard body section, said standard data covering the first portion and a complementary second portion of the body section, and
    subjecting the standard data to a registration process,
        wherein the model data is generated by adapting the standard data to the object data,
        said model data representing the first portion of the body section and the complementary second portion of the body section.

2. The method according to claim 1, wherein the step of providing the object data comprises:
    providing object raw data representing the body section; and
    creating masked object raw data by removing parts of the object raw data which represent portions of the body section being separated from the first portion.

3. The method according to claim 2, wherein the step of providing the object data further comprises subjecting the masked object raw data to a segmentation including at least one of a thresholding process, a filtering process, an edge detection, a contour detection and a shape matching process.

4. The method according to claim 1, wherein the step of providing the standard data comprises the step of selecting one of a plurality of standard data sets included in a standard data base.

5. The method according to claim 4, wherein the selecting step comprises the steps of:
    analyzing a similarity measure being characteristic for a matching degree between the object data and each of the plurality of standard data sets, and
    selecting the standard data set which provides best matching with the object data.

6. The method according to claim 1, wherein the step of providing the standard data comprises the step of constructing the standard data from at least two standard data sets included in a standard data base.

7. The method according to claim 1, wherein the registration process includes a rigid registration process including at least one of translating, rotating, scaling and shearing of the standard data, wherein rigid registration parameters are optimized using a gradient descent process.

8. The method according to claim 1, wherein the registration process includes a non-rigid registration process including a spatial transformation algorithm, wherein transform parameters are optimized using a gradient descent process.

9. The method according to claim 8, wherein the spatial transformation algorithm comprises a B-spline transformation.

10. The method according to claim 1, comprising the steps of:
collecting image data of the body section, and
providing the object data on the basis of the image data.

11. The method according to claim 1, wherein the object data comprise 3D CT or MR image data of the body section.

12. The method according to claim 1, comprising the step of constructing a virtual object model using the model data.

13. The method according to claim 1, comprising the step of constructing a real object model using the model data.

14. The method according to claim 1, comprising the step of subjecting the model data to a data adjustment based on a model data editing process.

15. The method according to claim 1, comprising the step of constructing an implant using the model data.

16. The method according to claim 1, comprising the step of subjecting the model data to at least one of recording, displaying, storing, and transmitting.

17. The method according to claim 1, comprising the step of visualization of the model data by 2D printing or 3D printing.

18. The method according to claim 1, wherein the body section comprises at least one of
a head or a part thereof,
a joint, and
soft tissue.

19. The method according to claim 18, wherein the joint is a knee.

20. A non-transitory computer-readable medium, with a program code for carrying out the method according to claim 1.

21. An apparatus comprising a non-transitory computer-readable storage medium containing program instructions for carrying out the method according to claim 1.

* * * * *